(12) United States Patent
Gjørsvik

(10) Patent No.: US 12,194,098 B2
(45) Date of Patent: Jan. 14, 2025

(54) METHOD FOR PREPARING A LIQUID PHARMACEUTICAL COMPOSITION AND DEVICE FOR USE IN SUCH METHOD

(71) Applicant: PHOTOCURE ASA, Oslo (NO)

(72) Inventor: Tore Gjørsvik, Gjerdrum (NO)

(73) Assignee: PHOTOCURE ASA, Oslo (NO)

( * ) Notice: Subject to any disclaimer, the term of this patent is extended or adjusted under 35 U.S.C. 154(b) by 1337 days.

(21) Appl. No.: 16/623,540

(22) PCT Filed: Jun. 21, 2018

(86) PCT No.: PCT/EP2018/066674
§ 371 (c)(1),
(2) Date: Dec. 17, 2019

(87) PCT Pub. No.: WO2018/234509
PCT Pub. Date: Dec. 27, 2018

(65) Prior Publication Data
US 2021/0145969 A1    May 20, 2021

(30) Foreign Application Priority Data

Jun. 21, 2017 (GB) ..................... 1709941
Oct. 26, 2017 (GB) ..................... 1717579

(51) Int. Cl.
| A61K 41/00 | (2020.01) |
| A61J 1/20 | (2006.01) |
| A61K 31/221 | (2006.01) |
| A61M 5/14 | (2006.01) |
| A61N 5/00 | (2006.01) |
| A61N 5/06 | (2006.01) |

(52) U.S. Cl.
CPC ........ *A61K 41/0061* (2013.01); *A61J 1/2086* (2015.05); *A61J 1/2089* (2013.01); *A61K 31/221* (2013.01); *A61M 5/1407* (2013.01); *A61M 2210/1085* (2013.01); *A61N 5/062* (2013.01)

(58) Field of Classification Search
CPC . A61K 41/0061; A61K 31/221; A61J 1/2086; A61J 1/2089; A61M 5/1407
See application file for complete search history.

(56) References Cited

U.S. PATENT DOCUMENTS 6,992,107 B1 * 1/2006 Gierskcky ............. C07C 229/22
514/506
7,217,736 B2 * 5/2007 Klaveness .......... A61K 41/0061
514/561
(Continued)

FOREIGN PATENT DOCUMENTS

| WO | WO-9316754 A1 * | 9/1993 | .......... A61M 5/1409 |
| WO | WO-2009109569 A2 * | 9/2009 | .......... A61B 5/0071 |
(Continued)

*Primary Examiner* — Guy K Townsend
(74) *Attorney, Agent, or Firm* — Fox Rothschild LLP

(57) ABSTRACT

The invention relates to a dissolution chamber (10) for use with a catheter for dissolving and preparing an aqueous solution of a water-soluble photosensitizing agent for installation into the bladder, e.g. for use in photodynamic diagnosis (PDD) or photodynamic therapy (PDT) of bladder cancer and to a method for preparing a liquid pharmaceutical preparation for delivery into a patient's bladder which includes the use of said dissolution chamber (10).

30 Claims, 4 Drawing Sheets

(56) References Cited

U.S. PATENT DOCUMENTS

| | | | | |
|---|---|---|---|---|
| 7,287,646 B2* | 10/2007 | Gierskcky | | A61K 49/0052 560/174 |
| 7,563,819 B1* | 7/2009 | Klaveness | | A61P 35/00 514/506 |
| 7,809,428 B2* | 10/2010 | Elmaleh | | A61K 41/0061 600/431 |
| 8,927,761 B2* | 1/2015 | Parent | | C07C 229/22 560/170 |
| 8,932,383 B2* | 1/2015 | Zhang | | C05F 11/02 71/21 |
| 9,249,086 B2* | 2/2016 | Brænden | | A61P 35/00 |
| 9,439,976 B2* | 9/2016 | Tung | | G01N 33/57484 |
| 2003/0055307 A1* | 3/2003 | Elmaleh | | A61K 41/0076 600/1 |
| 2003/0082105 A1* | 5/2003 | Fischman | | A61K 47/643 604/20 |
| 2004/0106679 A1* | 6/2004 | Klaveness | | A61P 35/00 514/561 |
| 2005/0107471 A1* | 5/2005 | Gierskcky | | C07C 229/22 514/550 |
| 2007/0258906 A1* | 11/2007 | Fischman | | A61N 5/062 424/9.71 |
| 2012/0136055 A1* | 5/2012 | Stensrud | | A61K 9/0034 514/561 |
| 2012/0144888 A1* | 6/2012 | Zhang | | C05F 11/02 71/23 |
| 2014/0010761 A1* | 1/2014 | Parent | | A61K 41/0061 424/463 |
| 2014/0227188 A1* | 8/2014 | Tung | | A61K 41/0061 530/331 |
| 2015/0191419 A1* | 7/2015 | Braenden | | A61K 41/0061 514/547 |
| 2020/0072842 A1* | 3/2020 | Vasilev | | G01N 33/57407 |
| 2021/0145969 A1* | 5/2021 | Gjorsvik | | A61K 31/221 |

FOREIGN PATENT DOCUMENTS

| | | | | |
|---|---|---|---|---|
| WO | WO-2012004399 A1 * | 1/2012 | | A61K 31/135 |
| WO | 2017/103105 A1 | 6/2017 | | |

* cited by examiner

METHOD FOR PREPARING A LIQUID PHARMACEUTICAL COMPOSITION AND DEVICE FOR USE IN SUCH METHOD

The invention relates to a dissolution chamber for use with a catheter for dissolving and preparing an aqueous solution of a water-soluble photosensitizing agent for installation into the bladder, e.g. for use in photodynamic diagnosis (PDD) or photodynamic therapy (PDT) of bladder cancer and to a method for preparing a liquid pharmaceutical preparation for delivery into a patient's bladder which includes the use of said dissolution chamber.

Bladder cancer is the ninth most common cancer diagnosis worldwide, with more than 330 000 new cases each year and more than 130 000 deaths per year. At any point in time, 2.7 million people have a history of urinary bladder cancer.

The diagnosis of bladder cancer ultimately depends on cystoscopic examination of the bladder (cystoscopy) and histological evaluation of the biopsy samples and/or resected tissue. In general, cystoscopy is initially performed in the office, using flexible instruments.

If a bladder tumor has been detected during cystoscopy, the patient will undergo transurethral resection (TUR), i.e. a procedure where the bladder is visualized through the urethra and tumors and lesions are resected.

As a standard procedure, cystoscopy and TUR are performed using white light. However, since the use of white light can lead to overlooking lesions that are present but difficult to detect, photodynamic diagnosis (PDD) is often used to improve such procedures. In general, PDD involves the administration of a photosensitizer or a precursor thereof (i.e. a "photosensitizing agent") to an area of interest. The photosensitizing agent is taken up into the cells, where a precursor of a photosensitizer is converted into a photosensitizer. Upon exposure of the area of interest to light of a suitable wavelength, the photosensitizer is excited and, upon relaxation to its ground state, fluorescence occurs, which is detected.

ALA-esters such as hexyl 5-ALA ester (hexaminolevulinate, HAL) and salts thereof are such precursors of photosensitizers. HAL preferably penetrates rapidly proliferating cells, e.g. tumor cells, where it is converted into porphyrins, such as protoporphyrin IX (PpIX), which are photosensitizers. Upon exposure to blue light, the porphyrins are exited and when relaxing to their ground state, energy in the form of red light is emitted. The red fluorescence enables specific and accurate visualization of tumor cells. Hexvix® (Photocure ASA, Norway) is a commercially available approved diagnostic agent that comprises HAL which is used in photodynamic diagnosis during cystoscopy and TUR procedures as an adjunct to white light.

Other photosensitizing agents have been used in PDD of bladder cancer, such as the precursor 5-aminolevulinic acid (5-ALA), see for example Babjuk et al., BJU Int 96(6), 2005, 798-802, or the photosensitizer PVP hypericin, see for example Straub et al., J. Endourol. 29(2), 2015, 216-222.

In PDD of bladder cancer, photosensitizing agents are used which are generally instilled into the bladder in the form of an aqueous solution via a catheter. The aqueous solution needs to be prepared on site by reconstituting the solid photosensitizing agent in an aqueous solvent/diluent just before instillation due to the limited stability of the photosensitizing agents in water.

Preparation on site is however cumbersome and hence impacts the commercial acceptance of a drug—health personnel generally prefer pharmaceutical compositions in a ready-to-use form as these are most convenient and allow for smooth logistics. Provision of ready-to-use forms also secures that drugs are prepared correctly with a reliable and accurate concentration of the active ingredient.

We have now surprisingly found a new alternative way to prepare an aqueous solution of a water-soluble photosensitizing agent for installation into the bladder, e.g. for use in PDD or PDT of bladder cancer, and components for use in such a preparation.

Hence, in a first aspect, the invention provides a method of preparing a liquid pharmaceutical composition for delivery into a patient's bladder via a urinary catheter, the method comprising:

a) providing in a dissolution chamber a solid water-soluble composition comprising a photosensitizing agent, wherein the dissolution chamber comprises (i) an inlet in fluid communication with a container comprising an aqueous solvent, (ii) an outlet in fluid communication with a catheter, and (iii) in a flow path between the inlet and the outlet said solid composition, and wherein the chamber is arranged to promote dissolution of the solid composition by the solvent within the chamber, b) flowing the solvent from the container into the dissolution chamber via the inlet;

c) obtaining a liquid composition by dissolving the solid composition in the solvent within the chamber, using the chamber and optionally a mixer to promote dissolution; and d) flowing the liquid composition out through the outlet into the catheter, which catheter is provided for delivery of the liquid composition into the patient's bladder.

In a second aspect the invention provides a dissolution chamber comprising an inlet to the chamber for fluid communication with a container comprising an aqueous solvent, an outlet from the chamber for fluid communication with a urinary catheter, and in a flow path between the inlet and the outlet a solid water-soluble composition comprising a photosensitizing agent, wherein the chamber is arranged to promote dissolution of the solid composition by the aqueous solvent within the chamber after the aqueous solvent enters the inlet and before the dissolved composition leaves the outlet.

In a preferred embodiment of the method and the chamber, the chamber is arranged such that during use the solid composition remains sealed within the chamber and fluid can only enter and leave the chamber via the inlet and the outlet.

The dissolution chamber of the invention/for use in the method of the invention can act as a drug delivery device. With such drug delivery device a composition comprising a photosensitizing agent can be supplied with the urinary catheter or a catheter device for PDT or PDD with the urinary catheter being a part of such a catheter device and the preparation of the aqueous solution of the composition occurs during normal use of the urinary catheter by instillation of the aqueous solvent through the drug delivery device rather than by instillation of a separately reconstituted aqueous solution of the composition. Thus, the composition can be supplied safely in a sealed drug delivery device along with the catheter device, which can be a single use device, with both dissolution and installation of the photosensitizing agent occurring through the addition of the aqueous solvent from a source of such a solvent, e.g. a syringe, infusion bag or the like. Any risk of contamination of the composition is reduced and the composition can always be supplied in the correct dosage for a given purpose, since the urinary catheter/the catheter device and composition can be packaged together for a specific use (e.g. diagnosis or treatment).

The term "photosensitizing agent" denotes photosensitizers or precursors of photosensitizers. The photosensitizing agent for use in the solid water-soluble composition may be a photosensitizing agent or a salt thereof, which is readily water-soluble. The term "pharmaceutically acceptable salt" denotes a salt that is suitable for use in a pharmaceutical product and which fulfils the requirements related to for instance safety, bioavailability and tolerability (see for instance P. H. Stahl et al. (eds.) Handbook of Pharmaceutical Salts, Publisher Helvetica Chimica Acta, Zurich, 2002).

Examples of photosensitizing agents are photosensitizers which are complexes of hypericin or pharmaceutically acceptable salts thereof with a polymeric complexing agent such as polyethylene glycol or poly-N-vinyl amide, e.g. polyvinylpyrrolidone (PVP). Preferred photosensitizers are PEG-hypericin or PVP-hypericin or sodium or potassium salts of PEG-hypericin or PVP-hypericin and in a more preferred embodiment the solid water-soluble composition comprises the sodium or potassium salt of PVP-hypericin.

Examples of precursors are 5-ALA and salts thereof or 5-ALA esters and salts thereof. Preferred 5-ALA esters are those of formula (I) or pharmaceutically acceptable salts thereof

wherein
$R^1$ represents an unsubstituted, straight-chained, $C_1$-$C_6$ alkyl group, preferably an unsubstituted, straight-chained $C_6$-alkyl group, i.e. hexyl-5-ALA ester.

Preferred pharmaceutically acceptable salts are acid addition salts with pharmaceutically acceptable organic or inorganic acids. Suitable acids include, for example, hydrochloric acid, nitric acid, hydrobromic acid, phosphoric acid, sulfuric acid, sulfonic acid and sulfonic acid derivatives, acetic acid, lactic acid, citric acid, tartaric acid, succinic acid, maleic acid, fumaric acid, ascorbic acid, oleic acid and stearic acid. Appropriate salts thus include, for example, hydrochloride, hydrobromide, nitrate, phosphate, sulfate, sulfonate, mesylate, tosylate, napsylate, acetate, lactate, citrate, tartrate, succinate, maleate, fumarate, ascorbate, oleate and stearate. Preferred acids are hydrochloric acid (HCl) and hydrobromic acid (HBr). Further preferred acids are nitric acid, sulfonic acid and sulfonic acid derivatives, e.g. methanesulfonic acid, naphthalenesulfonic acid or toluenesulfonic acids, as described in WO 2005/092838 to Photocure ASA, the entire contents of which are incorporated herein by reference. Most preferred salts are hydrochloride salts.

In a more preferred embodiment, the solid water-soluble composition comprises the hydrochloride salt of hexyl-5-ALA ester (HAL).

Complexes of hypericin or pharmaceutically acceptable salts thereof with a polymeric complexing agent such as polyethylene glycol or poly-N-vinyl amide are known in the art, they may be prepared e.g. as disclosed in WO 01/89576, WO 2017/054017 or WO 2017/054018, the entire contents of which are incorporated herein by reference.

5-ALA and 5-ALA esters and pharmaceutically acceptable salts thereof are known in the art, they may be prepared by any conventional procedure available in the art, e.g. as described in WO 96/28412, WO 02/10120 and WO 03/041673, the entire contents of which are incorporated herein by reference.

The solid water-soluble composition may be a sterile composition. It may be in the form of a powder, a film, a cake or granules or in a compressed form e.g. a compressed powder.

Advantageously, the composition may be a lyophilized composition. Such compositions are dissolved very easily, which means that a reliable concentration and dosage can be obtained via passage of the aqueous solvent through the dissolution chamber as described above. Moreover, sterile lyophilized compositions can be easily prepared, e.g. by sterile filtration of a solution of the composition prior to lyophilizing it, using a microfilter to remove contaminants such as microorganisms. Usually, a lyophilized cake or powder is obtained.

The solid water-soluble composition comprising a photosensitizing agent may further comprise common pharmaceutically excipients, such as salts, e.g. from an aqueous buffer which was used to dissolve the photosensitizing agent prior to lyophilization, or chelating agents like EDTA.

Alternatively, the solid water-soluble composition is a non-sterile composition and the dissolved composition is sterile-filtered prior to it being instilled into the patient's bladder. For that purpose, either the dissolution chamber or the urinary catheter or both may comprise a microfilter to remove contaminants and ensure that the dissolved composition which is instilled into the patient's bladder is sterile. If the microfilter is part of the dissolution chamber, such microfilter may be within the chamber or a part of the outlet.

If the solid water-soluble composition is a non-sterile composition, it may be in the form of a film or cake, e.g. obtained by solvent evaporation after synthesis of the photosensitizing agent: PVP-hypericin for instance can be obtained by dissolving hypericin in ethanol, followed by addition of PVP and water. After evaporation of the solvents a solid material is obtained.

The solid water-soluble composition may further be in the form of an effervescent tablet, powder or granules which are designed to quickly dissolve in the aqueous solvent and release a gas, usually carbon dioxide. Such effervescent compositions typically comprise a hydrogencarbonate and/or carbonate salt and an organic acid like citric acid, tartaric acid or malic acid. In contact with water, these excipients will generate carbon dioxide which will then be responsible for the rapid disintegration and dissolution of the composition in the aqueous solvent.

The container comprising the aqueous solvent for dissolving the solid composition is preferably a syringe or bag, e.g. an infusion bag. Typically, about 50 ml of the aqueous solvent is used to dissolve the solid composition.

The aqueous solvent is water or preferably an aqueous buffer. The aqueous solvent is preferably a sterile aqueous solvent.

If the photosensitizing agent is a complex of hypericin or pharmaceutically acceptable salts thereof with a polymeric complexing agent such as polyethylene glycol or poly-N-vinyl amide, e.g. polyvinylpyrrolidone (PVP), the aqueous solvent is preferably water, if an aqueous buffer, preferably a citric acid buffer or a phosphate buffer, was used to dissolve the photosensitizing agent prior to lyophilization. If water was used to dissolve the photosensitizing agent prior to lyophilization or the solid composition consists of the photosensitizing agent, the aqueous solvent is preferably an aqueous buffer, such as a citrate or phosphate buffer. The pH of the aqueous buffer is such that the dissolved solid composition is physiologically compatible.

If the photosensitizing agent is 5-ALA, the aqueous solvent is preferably an aqueous buffer, e.g. a carbonate/ bicarbonate buffer. The pH of the dissolved solid composition may be in the range of 4.8 to 6.5. If the photosensitizing agent is a 5-ALA ester, the aqueous solvent is preferably an aqueous buffer, e.g. a phosphate buffer. If the photosensitizing agent is the hydrochloride salt of HAL, the aqueous solvent is preferably a phosphate buffer, more preferably a phosphate buffer comprising disodium phosphate dehydrate, potassium dihydrogen phosphate, sodium chloride, hydrochloric acid, sodium hydroxide and water. The pH of the dissolved solid composition comprising a 5-ALA ester is range of 4.5 to 7.5, preferably in the range of 5.7 to 7.2.

The dissolution chamber of the invention/for use in the method of the invention may be manufactured with the composition enclosed therein.

With a lyophilized solid composition the dissolution chamber may consist of two parts with a first part arranged to receive the composition in a dissolved form sterile filtered and ready for lyophilization, and being open to the atmosphere so that lyophilization may proceed efficiently, and a second part forming an enclosure to the first part so that the dissolution chamber can be formed as a sealed unit around the lyophilized composition after lyophilization, with advantageously the only inlet and outlet to the dissolution chamber being the inlet and outlet mentioned above. Further, for a non-sterile solid composition in the form of a film, cake, powder, granule or tablet, e.g. an effervescent power, granule or tablet, the dissolution chamber may consist of two parts with a first part arranged to receive the solid composition and a second part forming an enclosure to the first part so that the dissolution chamber can be formed as a sealed unit around the solid composition.

Thus, the dissolution chamber may include a disc-shaped first part and a lid as the second part. The lid may also have a disc shape, or it may be a simple plate/disc shaped part. During manufacture the first part and the second part may be joined together in an irreversible fashion thereby forming the dissolution chamber as a sealed unit to contain the solid composition. The two parts may be joined by an adhesive or by fusing the two parts together, for example by fusing two plastic parts.

For non-sterile solid compositions, the material of the dissolution chamber is preferably a polymer, such as polyvinylchloride, polycarbonate, polypropylene, polyacryl, polyester or styrene copolymer such as methylmethacrylate acrylonitrile butadiene styrene or acrylonitrile butadiene styrene.

For lyophilized solid compositions, the dissolution chamber preferably consists of a single part. During manufacture, the outlet or inlet is closed with a stopper such that no liquid can leave the dissolution chamber through such outlet or inlet. The composition in a dissolved form ready for lyophilization is preferably sterile filtered into the dissolution chamber and lyophilized. After lyophilization, the opening of the inlet or outlet is also closed or sealed, such that the dissolution chamber comprises the sterile lyophilized composition.

For lyophilized solid compositions, the material of the dissolution chamber may be glass or a suitable polymer such as a polyolefine, preferably a polypropylene.

The outlet may include a filter for preventing transport of incompletely dissolved composition into the urinary catheter. Where the soluble composition is dissolved simply by movement of solvent between the inlet and outlet, the use of a filter can minimize the risk of inadvertently delivering undissolved composition into the bladder.

Generally, the flow rate of the aqueous solvent can be adjusted to fit the solubility of the solid composition by adjusting the diameter of the inlet and/or the outlet. The inlet and/or the outlet may have a cross-section arranged to provide a constrained rate of flow and/or to promote a required fluid pressure within the dissolution chamber. For example, the inlet may have a cross-section that is reduced compared to the usual cross-section of a catheter tubing to which it is attached in order to control the flow of fluid through the inlet. Alternatively and/or additionally the outlet may have a cross-section that is reduced compared to the usual cross-section of a catheter tubing to which it is attached in order to reduce the flow rate of fluid passing onward toward the patient's body and/or maintain an increased pressure in the dissolution chamber compared to the pressure of the fluid being passed onward to the patient's body. The outlet may have a cross-sectional area that is less than that of the inlet.

Typical sizes of urinary catheters are 10 F (3.3 mm) to 28 F (9.3 mm), preferably 15 F (5 mm) to 24 F (8 mm). The outlet diameter is preferably such that it fits to the diameter of the urinary catheter. The outlet is preferably a Luer lock or Luer slip which fits to a corresponding Luer lock or Luer slip on a catheter.

The outlet of the dissolution chamber is for fluid communication with a urinary catheter, preferably a urinary catheter within a catheter (device), e.g. a lumen within the catheter. In a preferred embodiment, the urinary catheter is fluidly connected to the outlet of the dissolution chamber for communication with the inside of the bladder.

The inlet is for fluid communication with a container comprising an aqueous solvent. In one embodiment, the container is fluidly connected to the inlet of the dissolution chamber either directly or via e.g. a tubing. For direct connection, the diameter of the inlet preferably fits to an outlet on the container. The inlet may be a Luer lock or Luer slip which fits to a corresponding Luer lock or Luer slip on the container comprising the aqueous solvent, e.g. syringe or bag.

The dissolution chamber may further comprise a mixer. The mixer is preferably held within the dissolution chamber and/or in the inlet. The mixer may include elements for inducing turbulence in the flow of aqueous solvent as it enters the chamber via the inlet, and/or for increasing at least one of the time of contact of the solvent with the solid composition, the shear force at the interface between the surface(s) of the solid composition and the flow of solvent, and/or the flow rate of the solvent adjacent to the surface(s) of the solid composition.

Advantageously, the mixer may comprise one or more static mixing element(s) such as vanes, baffles and/or convoluted flow paths. The solid composition may be shaped so that it forms a static mixing element as a part of the mixer. For example, the solid composition may be formed in the shape of a block with the urinary catheter lying inside such block and/or with a contoured surface, or the solid composition may be provided in multiple separate blocks with the urinary catheter lying between such blocks.

The mixer may alternatively or additionally include a dynamic element, for example a movable rotor or vane or other dynamic element with motion induced by the flow of solvent. One example embodiment includes a dynamic element in the form of a movable wall of the dissolution chamber enabling an increase in volume of the dissolution chamber as solvent is supplied to the chamber, with the outlet from the dissolution chamber being selectively closable to retain the solvent within the dissolution chamber, whereby repeated intake of and outlet of fluid from the dissolution chamber with variable volume results in turbulent mixing flow within the dissolution chamber. One possible arrangement of this type uses a dissolution chamber with a wall made of elastic material such that during intake of solvent the wall can expand in a manner similar to a balloon to increase the size of the dissolution chamber and during outlet of dissolved composition the wall returns elastically to its original configuration, decreasing the size of the dissolution chamber. This type of configuration requires intake and outlet of fluid rather than simple flow through the chamber, but it has the advantage of decreasing the risk of transport of incompletely dissolved composition through the outlet, since the outlet can be kept closed during the mixing/dissolution step.

Certain preferred embodiments will now be described by way of example only and with reference to the accompanying drawings in which.

Examples of dissolution chambers 10 are shown in FIGS. 1 to 5.

Figure 2:
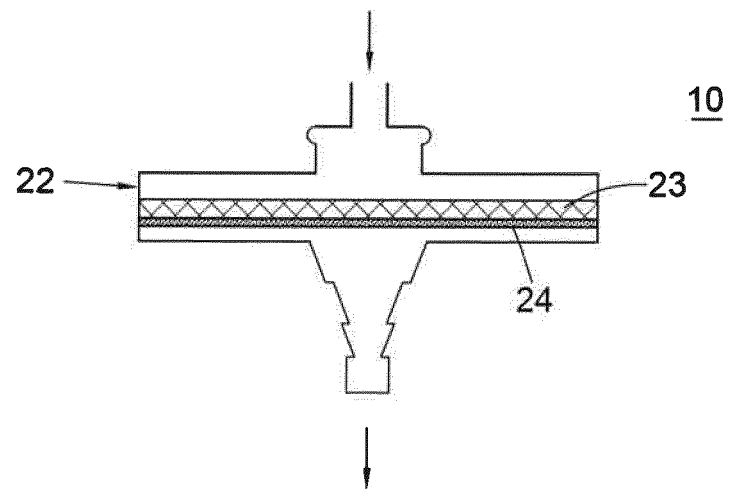
FIG. 2 is a cross sectional view of FIG. 1.
Figure 3:
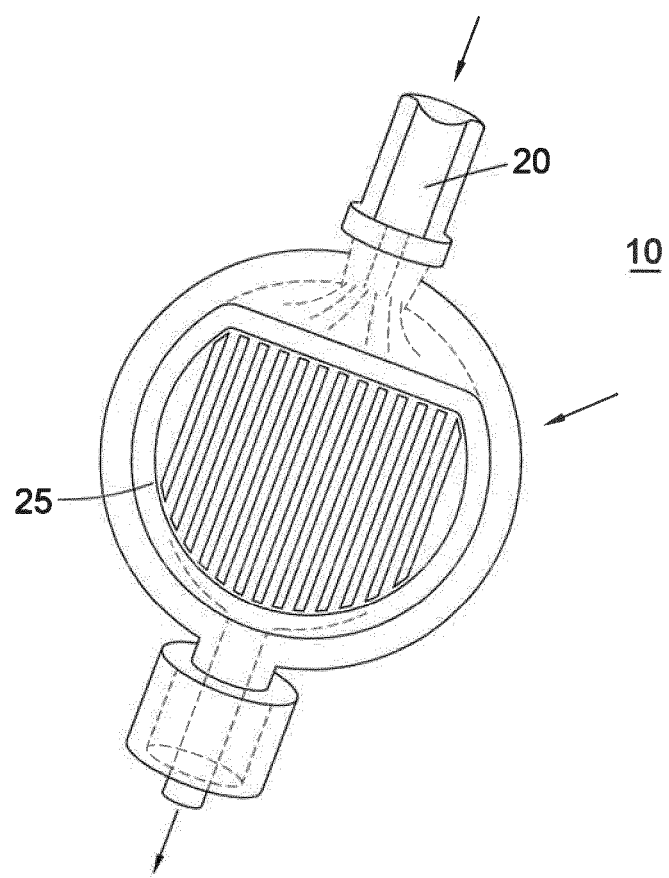

All three examples of the dissolution chamber 10 have the same basic features. An inlet 20 is arranged to receive the aqueous solvent from a source, i.e. a container such as a syringe or bag as explained above. The inlet 20 passes the solvent into a flow path inside the dissolution chamber (not shown) which contains the solid water-soluble composition comprising a photosensitizing agent. The fluid path may be the urinary catheter. The dissolution chamber 10 may further include a mixer (not shown) and the dissolution chamber along with the mixer are arranged to promote dissolution of the solid composition by aqueous solvent that enters the inlet 20. The dissolved composition then passes out of the dissolution chamber through the outlet 21 and onward to the urinary catheter, i.e. a catheter which is placed inside a patient's bladder, instilling the dissolved composition into the bladder. The inlet and outlet may be a Luer slip as shown in FIG. 1 or may have another suitable form, e.g. one as shown in FIG. 2 or FIG. 3.

This drug delivery method ensures that the composition comprising the photosensitizing agent can be supplied ready to be used with a catheter or as an integral part of a catheter or a catheter device such as a device for carrying out PDD or PDT in the bladder in a controlled manner and in sealed packaging. Unlike existing methods of preparing and providing lyophilized solid water-soluble compositions comprising a photosensitizing agent into a patient's bladder, it does not require "manual reconstitution", i.e. drawing up a solvent into a syringe, injecting the solvent into a vial comprising such a composition, mixing the composition and solvent within the vial, and then withdrawing the mixture into the syringe before using the syringe to then supply the dissolved composition to a catheter system. The dissolution chamber of the invention/the method of the invention does not require any transfer of solvent between different vessels and the solid composition is never readily accessible. Instead the composition is held within a sealed dissolution chamber, which can only receive and expel fluid via the inlet and outlet, and it is dissolved in this chamber before being passed directly into a patient's bladder without exposure to the outside.

Figure 1:
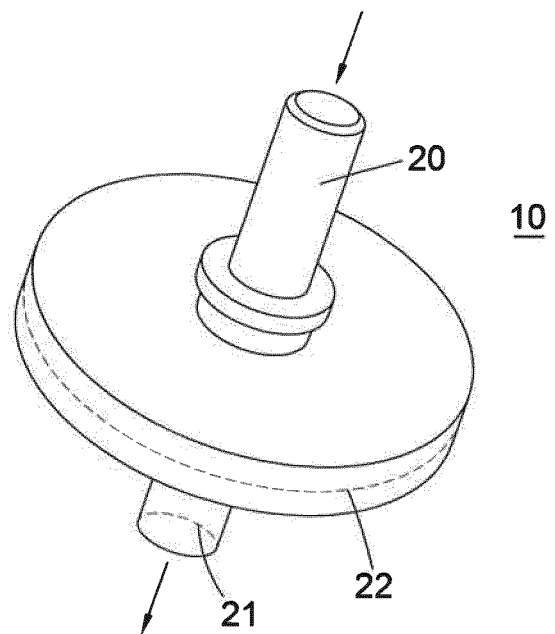
FIGS. 1 and 3 are perspective views of a first embodiment of a dissolution chamber.

The dissolution chamber 10 of FIG. 1 has a disc shape with the inlet 20 and outlet 21 being located along the axis of the disc. Within the disc-shaped part of dissolution chamber, a mixer such as vanes and baffles may direct the flow of solvent along and around the flow path with the solid composition. Upon intake of solvent into the inlet 20, it flows along/around the flow path thereby dissolving the composition before the fluid exits the outlet 21. Preferably, the solvent is injected rather than entering the inlet passively, e.g. by gravitational force.

The disc-shaped part is formed in two parts separated around the circumference of the disc as shown by the dotted line 22. The two parts are irreversibly sealed together once the solid composition, e.g. in the form of a powder, granule or tablet, e.g. an effervescent powder, granule or tablet, has been introduced into the chamber. Sealing can be achieved for example by the use of an adhesive or by thermally fusing plastic parts together.

Alternatively, the disc-shaped part is a single part (not shown). The photosensitizing agent in a dissolved form ready for lyophilization or a composition comprising the photosensitizing agent in a dissolved form ready for lyophilization is preferably sterile filtered into the dissolution chamber with the outlet 21 being sealed, e.g. by a stopper. Lyophilization is carried out with the liquid composition open to the atmosphere of the freeze-drier via the inlet 20. Alternatively, the inlet 20 is sealed, e.g. by a stopper, and lyophilization is carried out with the liquid composition open to the atmosphere of the freeze-drier via the outlet 21. Whether to seal the inlet or outlet may depend on various factors, e.g. the diameter, the length and the particular embodiment of said inlet and/or outlet.

FIG. 2 shows a cross-sectional view of a particular embodiment of FIG. 1, which includes a microfilter for sterile-filtration of the dissolved solid composition prior to it entering the urinary catheter. The inlet 20 is in the form of a Luer lock, the outlet 21 in the form of a hose barb connector. The disc-shaped dissolution chamber comprises the solid composition 23, e.g. in the form of a powder, granule or tablet, e.g. an effervescent powder, granule or tablet, which is located on top of a microfilter 24 suitable for sterile-filtering of the composition, once it has been dissolved and prior to leaving the outlet 21. The disc-shaped part is formed in two parts separated around the circumference of the disc as indicated (22). The two parts are irreversibly sealed together once the solid composition has been introduced into the chamber. Sealing can be achieved for example by the use of an adhesive or by thermally fusing plastic parts together.

The dissolution chamber of FIG. 3 has generally similar parts to that of FIG. 1, but instead of the inlet 20 and outlet 21 being located along the axis of a disc-shaped chamber they are located on opposite sides of the outer circumference of the disc. Solvent that enters the inlet 20 can flow along various passages in the flow path between the inlet and the outlet 21, here a Luer lock, as shown by the dotted lines 25, which are arranged to promote the dissolution of the solid composition. An example configuration uses several generally parallel passage ways. The dissolution chamber 10 of this Figure can be formed in the same way as that of FIG. 1, i.e. in one single or in two parts.

Figure 4:
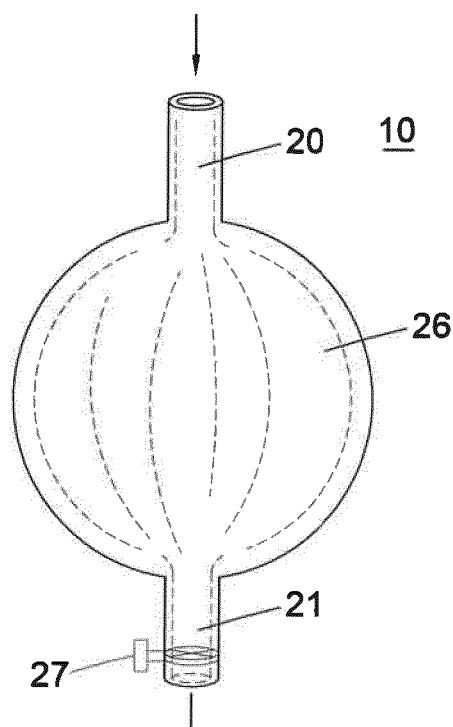
FIGS. 4 and 5 show front and plan view of another embodiment of a dissolution chamber.
Figure 5:
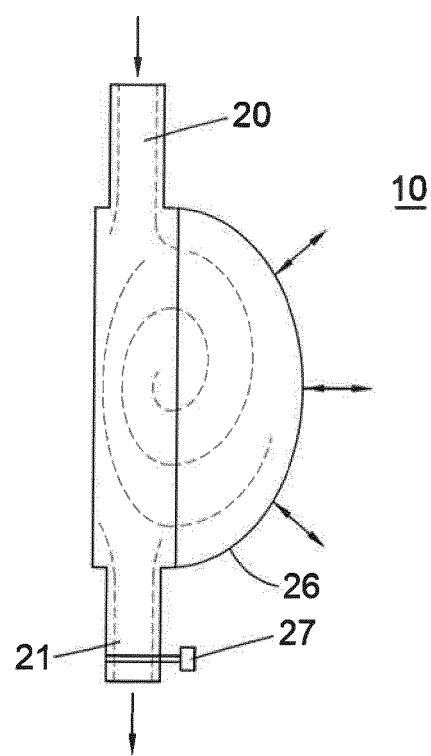
Figure 6:
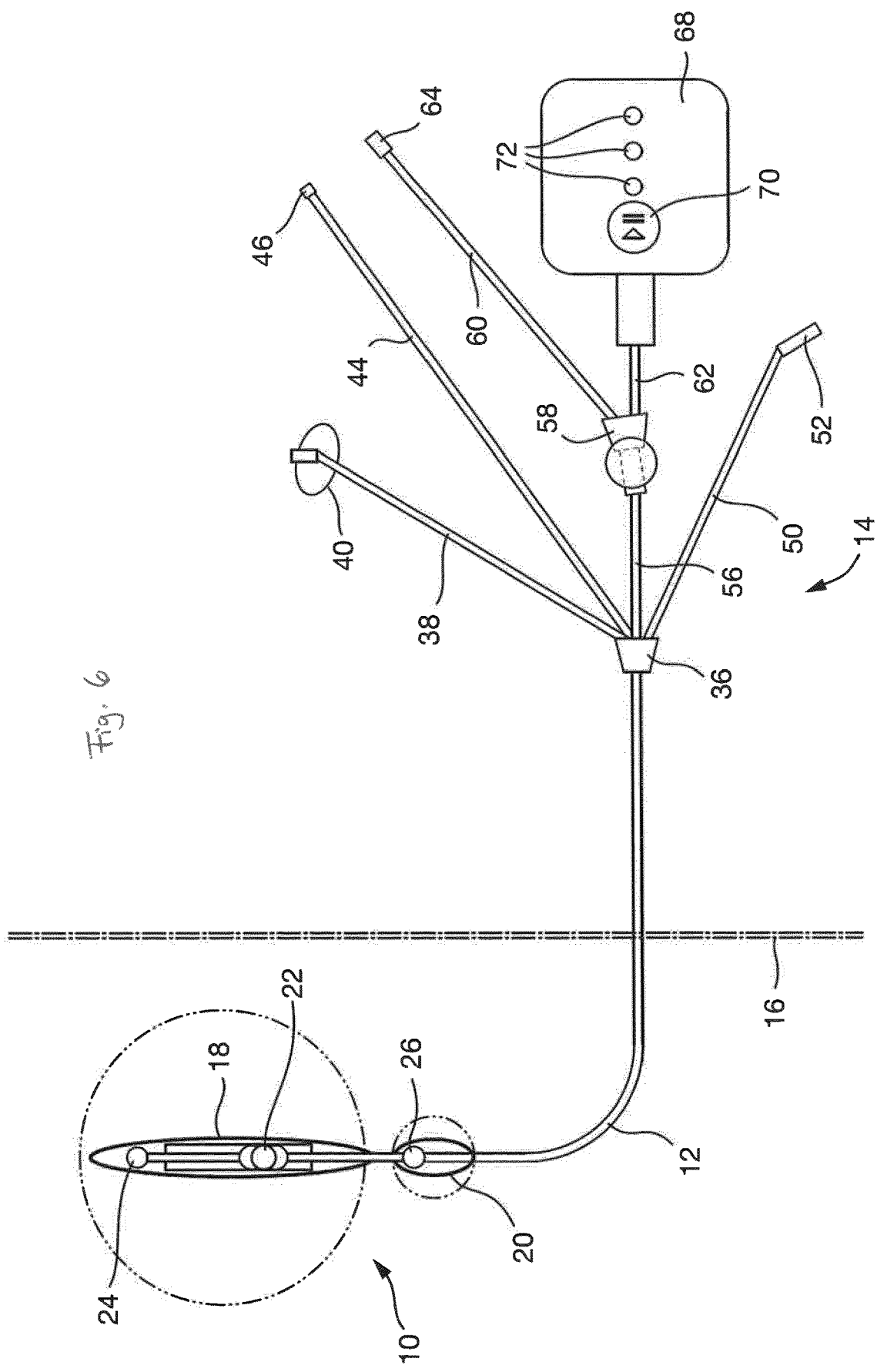
FIG. 6 shows the catheter PDT device of PCT/EP2016/081425

FIG. 4 and FIG. 5 show a further example for a dissolution chamber 10. The basic geometry of this chamber is similar to that of FIG. 3, i.e. disc-shaped having an inlet 20 and an outlet 21 which are located at opposite sides on the outer circumference of the disc. This embodiment differs from the earlier ones in that it has a flexible elastic wall 26 as well as a valve 27 for closing the outlet 21. The flexible elastic wall 26 can be made of an inert elastic polymer, e.g.

silicone. The valve 27 is used to close the outlet such that the composition cannot leave the chamber/enter the urinary catheter before it is completely dissolved. The elastic wall 26 allows for changes in volume of the dissolution chamber 10 when solvent is introduced/injected into it.

Dissolution of the solid composition with this dissolution chamber can be done simply by injecting solvent into via the inlet 20 into the chamber 10 and allowing time to pass. Alternatively, dissolution may be achieved by repeatedly injecting and then withdrawing solvent to generate turbulence within the chamber 10. When dissolution is completed, valve 27 is opened and the dissolved composition can be passed through the outlet 21 via the urinary catheter, e.g. a catheter or catheter device for PDD or PDT, into the patient's bladder. Operation of the valve and the delivery of solvent to the chamber could be manual, for example with a tap for the valve and a syringe for injecting and optionally withdrawing the solvent. Alternatively, such operation could be automated using an electrically actuated valve and a power injector.

An optional additional feature that could be present in any of the dissolution chambers discussed above is a filter in the outlet 21, either a microfilter to sterile-filter the dissolved composition before being instilled into a patient's bladder or a filter to remove any undissolved solid composition.

In a preferred embodiment the dissolution chamber is used with the catheter PDT device disclosed in WO 2017/103105 (Photocure ASA), the entire contents of which are incorporated herein by reference, for providing and instilling a dissolved photosensitizing agent for PDT of diseases and conditions in the bladder, e.g. for bladder cancer. The dissolution chamber may be an integral part of such catheter PDT device or may be used together with such a catheter PDT device.

The dissolution chamber 10 according to the invention can be mounted in-line with the first conduit 38 between the splitter 36 and the flush fluid connector 40 of the PDT device disclosed in FIGS. 1 and 2 of WO 2017/103105. In this arrangement the flush fluid connector 40 could be permanently or temporarily connected to the container comprising the aqueous solvent, which might be an infusion bag relying on gravitational force for fluid inlet into the dissolution chamber or preferably a syringe to push the solvent into the dissolution chamber. It should be noted that if the dissolution chamber of FIG. 4 and FIG. 5 is used, it would be necessary to use e.g. a syringe or any other means which allows to both supply and withdraw fluid.

Various embodiments of the dissolution chamber according to the invention are as follows:

Embodiment 1: A dissolution chamber comprising (i) an inlet for fluid communication with a container comprising an aqueous solvent, (ii) an outlet for fluid communication with a urinary catheter, and in a flow path between the inlet and the outlet a solid water-soluble composition comprising a photosensitizing agent, wherein the chamber is arranged to promote dissolution of the solid composition by the aqueous solvent within the chamber after the aqueous solvent enters the inlet and before the dissolved composition leaves the outlet.

Embodiment 2: The dissolution chamber according to embodiment 1, where in the chamber is arranged such that during use the solid composition remains sealed within the chamber and fluid can only enter and leave the chamber via the inlet and the outlet.

Embodiment 3: The dissolution chamber according to embodiments 1 or 2, wherein the flow passage is a urinary catheter Embodiment 4: The dissolution chamber according to embodiments 1 to 3, wherein the solid water-soluble composition comprises a complex of hypericin or a pharmaceutically acceptable salt thereof with a polymeric complexing agent.

Embodiment 5: The dissolution chamber according to embodiment 4, wherein the polymeric complexing agent is polyethylene glycol or poly-N-vinyl amide, preferably polyvinylpyrrolidone (PVP).

Embodiment 6: The dissolution chamber according to embodiment 5, wherein the solid water-soluble composition comprises PEG-hypericin or PVP-hypericin or a sodium or potassium salt of PEG-hypericin or PVP-hypericin.

Embodiment 7: The dissolution chamber according to embodiment 6, wherein the solid water-soluble composition comprises the sodium or potassium salt of PVP-hypericin.

Embodiment 8: The dissolution chamber according to embodiments 1 to 3, wherein the solid water-soluble composition comprises 5-ALA or a 5-ALA ester or a salt thereof.

Embodiment 9: The dissolution chamber according to embodiment 8, wherein the solid water-soluble composition comprises a 5-ALA ester of formula (I) or a pharmaceutically acceptable salt thereof

wherein
$R^1$ represents an unsubstituted, straight-chained, $C_1$-$C_6$ alkyl group.

Embodiment 10: The dissolution chamber according to embodiment 9, wherein the solid water-soluble composition comprises hexyl-5-ALA ester or a pharmaceutically acceptable salt thereof.

Embodiment 11: The dissolution chamber according to embodiment 10, wherein the solid water-soluble composition comprises the hydrochloride salt of hexyl-5-ALA.

Embodiment 12: The dissolution chamber according to embodiments 1 to 11, wherein the solid water-soluble composition is a sterile composition Embodiment 13: The dissolution chamber according to embodiments 1 to 12, wherein the solid water-soluble composition is in the form of a powder, a film, a cake or granules or in a compressed form.

Embodiment 14: The dissolution chamber according to embodiment 13, wherein the solid water-soluble composition is a lyophilized composition.

Embodiment 15: The dissolution chamber according to embodiment 14, wherein said dissolution chamber consists of a single part.

Embodiment 16: The dissolution chamber according to embodiment 15, wherein the material of said dissolution chamber is glass or a polymer such as a polyolefine, preferably a polypropylene.

Embodiment 17: The dissolution chamber according to embodiments 1 to 11, wherein the solid water-soluble composition is a non-sterile composition.

Embodiment 18: The dissolution chamber according to embodiment 17, wherein said dissolution chamber and/or the flow passage comprise a microfilter for sterile filtration of the dissolved composition.

Embodiment 19: The dissolution chamber of embodiment 18, wherein said microfilter is part of the dissolution chamber and is within the chamber or a part of the outlet.

Embodiment 20: The dissolution chamber of embodiments 17 to 19, wherein the solid water-soluble composition is obtained by solvent evaporation after synthesis of the photosensitizing agent.

Embodiment 21: The dissolution chamber of embodiments 17 to 19, wherein the solid water-soluble composition is in the form of an effervescent tablet, powder or granules.

Embodiment 22: The dissolution chamber according to embodiments 17 to 21, wherein the dissolution chamber consists of two parts with a first part arranged to receive the solid composition and a second part forming an enclosure to the first part so that the dissolution chamber can be formed as a sealed unit around the solid composition.

Embodiment 23: The dissolution chamber according to embodiments 17 to 22, wherein the material of the dissolution chamber is a polymer.

Embodiment 24: The dissolution chamber according to embodiment 23, wherein the polymer is polyvinylchloride, polycarbonate, polypropylene, polyacryl, polyester or styrene copolymer.

Embodiment 25: The dissolution chamber according to embodiments 1 to 24, wherein the aqueous solvent is water or preferably an aqueous buffer.

Embodiment 26: The dissolution chamber according to embodiment 25, wherein the aqueous solvent is a sterile aqueous solvent.

Embodiment 27: The dissolution chamber according to embodiments 1 to 26, wherein the outlet includes a filter for preventing transport of incompletely dissolved composition into the flow passage.

Embodiment 28: The dissolution chamber according to embodiments 1 to 27, wherein said dissolution chamber further comprises a mixer.

Embodiment 29: The dissolution chamber according to embodiment 28, wherein the mixer is held within the dissolution chamber and/or in the inlet.

Embodiment 30: The dissolution chamber according to embodiments 28 or 29, wherein the mixer includes elements for inducing turbulence in the flow of fluid as it enters the chamber via the inlet, and/or for increasing at least one of the time of contact of the solvent with the solid composition, the shear force at the interface between the surface(s) of the solid composition and the flow of solvent, and/or the flow rate of the solvent fluid adjacent to the surface(s) of the solid composition.

Embodiment 31: The dissolution chamber according to embodiments 28 to 30, wherein the mixer comprises one or more static mixing element(s)

Embodiment 32: The dissolution chamber according to embodiment 31, wherein the mixer comprises one or more vanes, baffles and/or convoluted flow paths.

Yet another aspect of the invention is a kit comprising a dissolution chamber as described herein and a container comprising an aqueous solvent suitable for dissolving the water-soluble solid composition comprising a photosensitizing agent comprised in the dissolution chamber. Suitable container and aqueous solvents and preferred embodiments of such containers and solvents have been discussed before. The container may be fluidly connected to the dissolution chamber via the inlet on the dissolution chamber or via a tube which is fluidly connected to the container and the inlet.

In another embodiment, the kit optionally further comprises a urinary catheter for fluid connection to the outlet of the dissolution chamber, such catheter is for installation of fluids into the bladder. The dissolution chamber may be connected to the urinary catheter prior to use or may be an integral part of the device. If the dissolution chamber is connected to the device prior to use, said dissolution chamber and/or the urinary catheter preferably comprise a sterile-filter to ensure that the dissolved composition is sterile before being instilled into a patient's bladder.

In yet another embodiment, the kit comprises a dissolution chamber as described, the catheter PDT device disclosed in WO 2017/103105 and a optionally a container comprising an aqueous solvent suitable for dissolving the water-soluble solid composition comprising a photosensitizing agent comprised in the dissolution chamber. The dissolution chamber may be connected to the catheter PDT device prior to use or may be an integral part of the device. If the dissolution chamber is connected to the device prior to use, said dissolution chamber and/or the catheter PDT device preferably comprise a sterile-filter to ensure that the dissolved composition is sterile before being instilled into a patient's bladder.

The invention claimed is:

1. Method of preparing a liquid pharmaceutical composition for delivery into a patient's bladder via a urinary catheter, the method comprising:
    a) providing in a dissolution chamber a solid water-soluble composition comprising a photosensitizing agent, wherein the dissolution chamber comprises (i) an inlet in fluid communication with a container comprising an aqueous solvent, (ii) an outlet in fluid communication with a catheter, and (iii) in a flow path between the inlet and the outlet said solid composition, and wherein the chamber is arranged to promote dissolution of the solid composition by the solvent within the chamber,
    b) flowing the solvent from the container into the dissolution chamber via the inlet;
    c) obtaining a liquid composition by dissolving the solid composition in the solvent within the chamber, using the chamber and optionally a mixer to promote dissolution; and
    d) flowing the liquid composition out through the outlet into the catheter, which catheter is provided for delivery of the liquid composition into the patient's bladder.

2. The method according to claim 1, wherein the chamber is arranged such that the solid composition remains sealed within the chamber and solvent can only enter and leave the chamber via the inlet and the outlet.

3. The method according to claim 1, wherein the solid water-soluble composition comprises a complex of hypericin or a pharmaceutically acceptable salt thereof with a polymeric complexing agent, and wherein the polymer complexing agent is polyethylene glycol (PEG).

4. The method according to claim 1, wherein the solid water-soluble composition comprises 5-ALA or a 5-ALA ester or a salt thereof.

5. The method according to claim 4, wherein the solid water-soluble composition comprises a 5-ALA ester of formula (I) or a pharmaceutically acceptable salt thereof

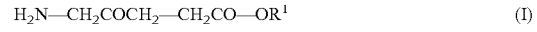

$$H_2N-CH_2COCH_2-CH_2CO-OR^1 \quad (I)$$

wherein
    $R^1$ represents an unsubstituted, straight-chained, $C_1$-$C_6$, alkyl group.

6. The method according to claim 5, wherein the solid water-soluble composition comprises hexyl-5-ALA ester or a pharmaceutically acceptable salt thereof.

7. The method according to claim 6, wherein the solid water-soluble composition comprises the hydrochloride salt of hexyl-5-ALA.

8. The method according to claim 1, wherein the solid water-soluble composition is a sterile composition.

9. The method according to claim 1, wherein the solid water-soluble composition is in the form of a powder, a film, a cake or granules or in a compressed form.

10. The method according to claim 9, wherein the solid water-soluble composition is a lyophilized composition.

11. The method according to claim 1, wherein the dissolution chamber is made of a material selected from glass or a polymer.

12. The method according to claim 1, wherein the solid water-soluble composition is a non-sterile composition.

13. The method according to claim 12, wherein the dissolution chamber and/or the catheter comprise a microfilter for sterile filtration of the liquid composition.

14. The method according to claim 13, wherein said microfilter is part of the dissolution chamber and is within the chamber or is a part of the outlet.

15. The method according to claim 12, wherein the dissolution chamber consists of two parts with a first part arranged to receive the solid composition and a second part forming an enclosure to the first part so that the dissolution chamber can be formed as a sealed unit around the solid composition.

16. The method according to claim 12, wherein the dissolution chamber is made of a polymer.

17. The method according to claim 16, wherein the polymer is polyvinylchloride, polycarbonate, polypropylene, polyacryl, polyester or styrene copolymer.

18. The method according to claim 1, wherein the aqueous solvent is water or an aqueous buffer.

19. The method according to claim 1, wherein the aqueous solvent is a sterile aqueous solvent.

20. The method according to claim 1, wherein the outlet includes a filter for preventing transport of incompletely dissolved composition into the catheter.

21. The method according to claim 1, wherein the dissolution chamber further comprises a mixer.

22. The method according to claim 21, wherein the mixer is held within the dissolution chamber and/or in the inlet.

23. The method according claim 21, wherein the mixer includes elements for inducing turbulence in the flow of solvent as it enters the chamber via the inlet, and/or for increasing at least one of (i) the time of contact of the solvent with the solid composition, (ii) the shear force at the interface between the surface(s) of the solid composition and the flow of solvent, and/or (iii) the flow rate of the solvent adjacent to the surface(s) of the solid composition.

24. The method according to claim 21, wherein the mixer comprises one or more static mixing element(s).

25. The method according to claim 24, wherein the mixer comprises one or more vanes, baffles and/or convoluted flow paths.

26. The method according to claim 1, wherein the solid water-soluble composition comprises hexyl-5-ALA ester or a pharmaceutically acceptable salt thereof, the aqueous solvent is a phosphate buffer, and the pH of the dissolved solid composition is in the range of 4.5 to 7.5.

27. The method according to claim 26, wherein the solid water-soluble composition is a sterile, lyophilized composition.

28. The method according to claim 11, wherein the polymer is a polyolefine.

29. The method according to claim 28, wherein the polyolefine is a polypropylene.

30. The method according to claim 26, wherein the solid water-soluble composition comprises the hydrochloride salt of hexyl 5-ALA ester, the aqueous solvent is a phosphate buffer comprising disodium phosphate dihydrate, potassium dihydrogen phosphate, sodium chloride, hydrochloric acid, sodium hydroxide and water and the pH of the dissolved solid composition is in the range of 5.7 to 7.2.

* * * * *